(12) United States Patent
Maynard

(10) Patent No.: US 9,420,795 B2
(45) Date of Patent: Aug. 23, 2016

(54) GLYCOLATE FORMULATION FOR PRESERVING WOOD AND LIKE MATERIALS

(75) Inventor: Nigel Paul Maynard, West Harbour (NZ)

(73) Assignee: Matterworks One Limited, Albany (NZ)

( * ) Notice: Subject to any disclaimer, the term of this patent is extended or adjusted under 35 U.S.C. 154(b) by 25 days.

(21) Appl. No.: 14/234,548

(22) PCT Filed: Jul. 27, 2012

(86) PCT No.: PCT/IB2012/053836
§ 371 (c)(1),
(2), (4) Date: May 5, 2014

(87) PCT Pub. No.: WO2013/014644
PCT Pub. Date: Jan. 31, 2013

(65) Prior Publication Data
US 2014/0242137 A1 Aug. 28, 2014

Related U.S. Application Data

(60) Provisional application No. 61/512,241, filed on Jul. 27, 2011, provisional application No. 61/606,776, filed on Mar. 5, 2012.

(51) Int. Cl.
*A01N 55/02* (2006.01)
*A01N 59/20* (2006.01)
*A01N 25/02* (2006.01)
*A01N 37/36* (2006.01)
*B27K 3/34* (2006.01)

(52) U.S. Cl.
CPC ............ *A01N 55/02* (2013.01); *A01N 25/02* (2013.01); *A01N 37/36* (2013.01); *A01N 59/20* (2013.01); *B27K 3/34* (2013.01)

(58) Field of Classification Search
CPC ...... A01N 59/20; A01N 25/02; A01N 37/36; A01N 55/02; A01N 33/12; B27K 3/34
USPC ...... 425/405; 427/421.1, 429, 439; 514/494, 514/499
See application file for complete search history.

(56) References Cited

U.S. PATENT DOCUMENTS

| | | | |
|---|---|---|---|
| 4,544,761 A * | 10/1985 | Taylor et al. | ................. 556/130 |
| 4,620,990 A | 11/1986 | Dicker | |
| 4,876,278 A * | 10/1989 | Taylor | ................. A61K 31/045 514/494 |
| 4,929,454 A | 5/1990 | Findlay et al. | |
| 4,943,316 A | 7/1990 | Taylor | |
| 5,916,356 A | 6/1999 | Williams et al. | |
| 6,508,869 B2 | 1/2003 | Tseng et al. | |
| 7,674,481 B2 | 3/2010 | Leach et al. | |
| 8,425,980 B2 | 4/2013 | Maynard | |
| 9,023,428 B2 | 5/2015 | Maynard | |
| 2004/0248760 A1* | 12/2004 | Woodhead | ..................... 510/470 |
| 2006/0115506 A1 | 6/2006 | Harmer et al. | |
| 2006/0269583 A1 | 11/2006 | Garst et al. | |
| 2006/0288904 A1 | 12/2006 | Leach et al. | |
| 2007/0190177 A1* | 8/2007 | Kling et al. | ................... 424/641 |
| 2008/0199525 A1 | 8/2008 | Leach et al. | |
| 2009/0280345 A1 | 11/2009 | Maynard et al. | |
| 2010/0179339 A1 | 7/2010 | Dutta et al. | |
| 2012/0148857 A1* | 6/2012 | Smith | .................... B27K 3/163 428/537.1 |
| 2013/0136849 A1 | 5/2013 | Maynard | |

FOREIGN PATENT DOCUMENTS

| | | |
|---|---|---|
| EP | 0046380 | 2/1982 |
| NZ | 549510 | 6/2008 |
| WO | 9525513 | 9/1995 |
| WO | 2006851755 | 8/2006 |
| WO | 2008026941 | 3/2008 |

OTHER PUBLICATIONS

PCT/NZ2013/000034 International Search Report dated Jun. 3, 2013.
PCT/NZ2013/000034 International Preliminary Report on Patentability dated Sep. 9, 2014.
Fairlie et al., Agents Action, 1992, pp. 1552-158, vol. 36.
Hassan, Hazimah Abu; Characterisation and Reactions of Copper (II) Glycerol Complex, PhD Thesis, Universiti Putra Malaysia, 1998.
Kear, Gareth et al, Corrosion of Mild Steel, HDG Steel and 316 Stainless Stell in CCA, CuAz and ACQ-Treated Pinus Radiate, Conference Paper No. 114 Presented at 16th Intl Corrosion Congress, Beijing, China, 9/19-24/200.
Koyano, H. et al, Electroless Copper Plating from Copper-Glycerin Complex Solution, J. Electrochem Soc, Nov. 1992, vol. 139, No. 11.

* cited by examiner

*Primary Examiner* — Michael G Hartley
*Assistant Examiner* — Robert Cabral
(74) *Attorney, Agent, or Firm* — Honigman Miller Schwartz and Cohn LLP; Thomas A. Wootton, Esq.; Jonathan P. O'Brien

(57) ABSTRACT

Compositions and methods for use in treating, in particular, lignocellulosic substrates such as lumber, are provided; wherein said compositions comprise a preservative or biocidal species, other than boron, in the form of a glycolate. The methods may be used for the purpose of, for example, preventing the growth of pest organisms, or for providing other specific properties to the substrate.

17 Claims, 1 Drawing Sheet

GLYCOLATE FORMULATION FOR PRESERVING WOOD AND LIKE MATERIALS

PRIORITY

This application claims priority from PCT application PCT/IB2012/053836, filed on Jul. 27, 2012, which claims priority from U.S. provisional application 61/512,241, filed Jul. 27, 2011, and from U.S. provisional application 61/606,776, filed on Mar. 5, 2012, the entire contents of which are incorporated herein by cross-reference.

FIELD OF THE INVENTION

The present invention relates to compositions for use in treating organic substrates and to methods of delivering compositions to organic substrates. In particular, the present invention relates to compositions for treating and methods of delivering treatment compounds to lignocellulosic substrates, such as lumber. The methods may be used for the purpose of, for example, preventing the growth of pest organisms, or for providing specific properties to the substrate.

BACKGROUND

Lumber from many tree species lacks durability and frequently has inferior physical properties. These deficiencies are more common in lumber extracted from man-made plantation forests.

It is typical for lumber processors to alter lumber properties to improve durability and enhance physical properties, such as hardness, water repellence, and protection against attack by insects or fungi.

It is well known to those versed in the art that these deficiencies can be remedied to a greater or lesser extent by impregnating the lumber with preservatives, polymers, and the like. Impregnation processes have been used for many decades. Most involve impregnation with treating fluids.

Typically the lumber is treated with waterborne preservatives or with solvent fluids based on non-polar organic solvents, such as white spirits (LOSP processes). Both processes are similar in that variations of vacuum and pressure are used.

When treating organic substrates it is essential that at least some of the biocide is available to attack the micro-organism—at least some of the biocide must be soluble. There is a compromise between achieving a very low level of solubility for health, safety and environmental reasons and retaining a level of solubility necessary for bioperformance.

It is known to those versed in the art of wood preservation that fungi attack substrates by a number of means including, for example, the production of extracellular compounds such as hydroxyl radicals, peroxides, strong acids, and the like. Some fungi produce extracellular oxalic acid, which can precipitate copper compounds and the like frequently used as wood preservatives, even at quite low pH. Once precipitated by oxalate the copper is no longer biologically active.

Historically one of the most important waterborne preservatives was CCA (copper chrome arsenate). However, arsenic is highly poisonous and the form of chromium used is carcinogenic.

Over the past two decades chromium and arsenic have in many instances been replaced by quaternary ammonium compounds, but because chromium was no longer present another method was required to solubilise the copper. One method involves use of large amounts of ammonia or organic amine compounds. Ammonia is a toxic gas and an environmental pollutant and organic amines are expensive. The use of these compounds is also wasteful, since most of such compounds are simply eluted from the wood after treatment. The preservative would be more competitive if these issues could be mitigated.

Preservatives based on copper solubilised using ammonia or amines are known generically as ACQ or copper azole. The preservatives typically contain a co-biocide based on a quaternary ammonium compound or an azole such as tebuconazole or propiconazole. The pH is typically around 10.5 to 11. The quaternary ammonium compound traditionally carried a halogen counter ion such as chloride, but in recent years this has been replaced by carbonate to reduce corrosion. Carbonate based quaternary ammonium compounds are more expensive therefore any means of reducing the amount used will provide value.

Important issues arise from the use of ammonia or amines. The ammonia or amines are critical to maintaining copper in solution. However, subsequent to treatment, residual ammonia or amines cause leaching of the copper from the wood. Leaching reduces wood loading and can potentially lead to failure of the wood. This issue can be addressed by increasing the initial loading in the wood at additional cost. Leaching of copper into the environment is, however, also problematic.

Another issue arising from the use of copper compounds solubilised by ammonia or amines is the corrosion of steel componentry used during installation of the treated wood. The corrosion is due to the soluble copper reacting directly with the steel. This has necessitated use of stainless steel fittings and fixtures which adds to cost. Corrosion has been mitigated to some extent by using halogen free compositions, but still remains an issue.

Another issue arising from the use of ammonia and/or amines is that these compounds provide a nitrogen source and thus encourage growth of disfiguring mould on the lumber surface.

Later versions of ACQ utilise amines. In earlier versions ammonia was used, but the excess ammonia released from the composition or the treated wood was a hazard to the health and safety of workers and the environment. Despite this ammonia remains in use for refractory wood species such as those encountered in Australia and the west of the United States because it facilitates penetration of treating compositions into these species.

The ratio of ammonia and/or amine or mixtures thereof to copper in the treating solution is typically a stoichiometric ratio of 4:1 of amine or ammonia to copper but this may be increased further to maintain solution stability. This is specified in standards such as AWPA P5-95 ACQ Type D.

The compound formed in the preservative solution is a tetraamine complex, for example, $Cu(NH_3)_4$, when ammonia is used—such ligand might be called a hard ligand.

A number of researchers have reported that the optimum ratio after treatment of the wood for best biological performance is a stoichiometric ratio of 1:1 of copper to ammonia or amine subsequent to leaching. This indicates that 75 percent of the solubilising agent is lost during leaching. The excess amine or ammonia is lost at a cost, and copper is also leached. If such leaching could be mitigated it would provide considerable benefit in terms of cost and safety.

U.S. Pat. No. 4,929,454 reports compositions containing copper compounds solubilised with ammonia and which include quaternary ammonium compounds.

U.S. Pat. No. 5,916,356 reports compositions containing copper compounds and azoles.

During the past decade a number of copper based preservatives that are not only free of chromium and arsenic but also free of ammonia and amines have been developed. This is achieved by converting the otherwise insoluble copper based biocide into a form in which the particle size is between around 100 and 1000 nanometers. Particles of this size are sufficiently small that, when impregnated using standard techniques, they can fully penetrate into the substrate. This approach mitigates the issues of leaching and cost due to the ammonia or amines.

However, these nano biocides have their own issues.

US 2008/0199525 reports the use of micronized biocides as wood preservatives. The biocides are prepared by milling using the likes of zirconia balls. The nano biocides are designed to eliminate the inclusion of costly and potentially toxic components, such as ammonia or amines.

Similarly, WO 2007/002156 reports a wood preservative prepared by grinding biocides in a ball mill in the presence of suitable dispersants. The use of dispersants prevents the particle size increasing through a process known as Ostwald ripening. Frequently, high loadings of dispersants are required to prevent agglomeration and settling of particles in sub-micron compositions. The use of dispersants increases the overall cost of the composition, particularly when high loadings are required.

US 2008/0199525 reports a reduction in the leaching of copper from treated wood samples by a factor of around 90 percent. This has cost and environmental benefits.

US 2008/0199525 reports a broad range of co-biocides which we incorporate herein by reference.

Claims are made commercially that the micronized copper based preservative systems are significantly less corrosive than the aforementioned ACQ types, including those based on halogen free quaternary ammonium compounds. Accordingly, in many service situations galvanised steel fixtures can be used, whereas stainless steel fixtures must be used in contact with ACQ treated wood. The reason for this is that micronized products have very low solubility and thus do not interact as corrosively.

Milling or grinding processes, however, have associated problems. On a commercial scale, equipment is capital intensive and can cost overall several million dollars. Energy costs may be high, cooling costs may be high and replacement grinding media is expensive. In addition, costly dispersants and surfactants may also be required.

Due to the capital required, plants need to be large and focus manufacture in key locations. This allows higher throughput to amortise capital costs, but can lead to high transport costs for the finished products to geographically remote users.

In addition, grinding is a very slow process, which exacerbates manufacturing times.

It can be seen that developments tend to mitigate problems but, frequently, at an additional cost.

Industry is striving to reduce the impact of compositions on workers and the environment without increasing costs.

It would be valuable to industry if the leaching, corrosion and mould issues could be mitigated without increasing cost or if at least an alternative to those currently available could be provided.

Typically micronized copper compounds include the likes of cupric hydroxide or basic copper carbonate. These compounds are generally prepared by the reaction of an alkali hydroxide or alkali carbonate with cupric sulphate. Cupric sulphate is one of the primary feeds in copper chemistry. But the step of converting the cupric sulphate to cupric hydroxide or carbonate introduces another process and cost.

In some circumstances cupric oxide can be used and when prepared by a direct oxidation route can be more competitive than cupric hydroxide or basic copper carbonate.

It is interesting to note that glycols have been used for many years in the preparation of boron containing biocides. NZ 549510 provides an extensive description of spiroboronate chemistry relating to the manufacture of soluble boron species using glycols, which is incorporated herein by reference.

EP 0046380 reports "a hygroscopic liquid carrier for application to a porous substrate such as timber wherein the composition contains at least 20% equivalent of boric oxide". The use of various boron compounds is reported. The preferred embodiment uses disodium octaborate. A range of glycols are also reported. The preferred embodiment uses ethylene glycol. There is no mention of the chemistry involved, but it is likely that at least some spiroboronate or glycolate is formed.

U.S. Pat. No. 4,620,990 reports "a method of impregnating a wooden structure by diffusion of boric acid wherein solid rods of disodium octaborate are supplemented by an hygroscopic liquid which can be a glycol".

U.S. Pat. No. 6,508,869 reports "a composition comprising an amine oxide and a boron compound." This combination is designed to enhance penetration of boron compounds into lumber.

Those versed in the art will be aware that boric acid compounds, including borates and octaborates, form spiroboronate complexes with vicinal diols, such as glycols, and that in an aqueous medium this substantially reduces pH. This is typified in analytical chemistry wherein mannitol is added to borate solutions to allow the borate to be titrated as a strong acid.

Those versed in the art will be aware of the composition and structure of spiroboronates. An example is shown below (Spiroboronate Example 1). Borates can also form partial spiroboronates. An example is also shown below (Spiroboronate Example 2).

Spiroboronate Example 1

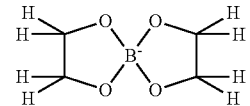

Spiroboronate Example 2

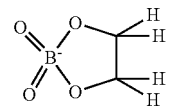

Spiroboronates can also be called glycolates. That is, compounds of boron with glycol wherein one or more labile hydrogen atoms of the glycol is replaced by a bond directly between the boron atom and an oxygen atom of the glycol.

The term glycolate as used herein means a compound of a glycol and a reactive species such as copper or boron. It should not be confused with a salt of glycolic acid. The glycolates described herein relate to compounds formed without requirement for carboxylic acid functionality.

Practitioners have also endeavoured to preserve substrates by inclusion of silicon or aluminium compounds.

US 2006/0115506 reports the incorporation of silicon or aluminium as colloidal particles. However these elements are incorporated as nano particles and so incur the same issues described above. A wide range of co-biocides are also reported, which we hereby incorporate by reference.

WO 2006/081755 reports the use of silica emulsion to preserve wood.

US 2006/0269583 reports the use of silicon and aluminium containing preservatives wherein the elements are in soluble form. The preservatives are acidic and are therefore incompatible with the likes of ACQ, copper azole or similar such compositions.

The compositions described above are not compatible with the likes of current alternatives and therefore provide only a partial solution to current issues.

U.S. Pat. No. 4,943,316 reports the manufacture of a number of metal glycolates aided by the use of microwave energy, which we incorporate herein by reference.

US 2010/0179339, which we incorporate herein by reference, reports the preparation of glycolates of a range of species for use as fire retardants.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

OBJECT

It is an object of the present invention to provide a composition for delivery to organic substrates, particularly lignocellulosic substrates, which may have a preserving or modifying effect on the substrate; and/or at least to provide the public with a useful choice.

SUMMARY OF INVENTION

In one aspect, the present invention is a composition for treating an organic substrate comprising:
 a liquid carrier; and
 a preservative or biocidal or substrate modifying species, other than boron, in the form of a glycolate;
 wherein the pH of the composition is such that the glycolate is at least partially soluble in the liquid carrier.

The following embodiments relate to the aspect above and any of the aspects described below, where appropriate.

In one embodiment, the pH of the composition is greater than 7.

In some embodiments, the pH of the composition is 8 or more, 9 or more, 10 or more, or 11 or more.

In one embodiment, the pH of the composition is about 11.

In some embodiments, the pH of the composition is from 7 to 14, from 7 to 13, from 7 to 12, or from 7 to 11. In some embodiments, the pH of the composition is from 8 to 14, from 8 to 13, from 8 to 12, or from 8 to 11. In some embodiments, the pH of the composition is from 9 to 14, from 9 to 13, from 9 to 12, or from 9 to 11. In some embodiments, the pH of the composition is from 10 to 14, from 10 to 13, from 10 to 12, or from 10 to 11.

In one embodiment, the pH of the composition is less than 7.

In some embodiments, the pH of the composition is 6 or less, 5 or less, 4.5 or less, 4 or less, or 3 or less.

In some embodiments, the pH of the composition is from 3 to 7 or from 4 to 7. In some embodiments, the pH of the composition is from 3 to 6 or from 4 to 6. In some embodiments, the pH of the composition is from 3 to 5 or from 4 to 5. In some embodiments, the pH of the composition is from 3 to 4.5. In some embodiments, the pH of the composition is 3 to 4. In some embodiments, the pH of the composition is from 4 to 4.5.

In one embodiment, the pH of the composition is less than 4.5. In one embodiment, the pH of the composition is less than 4. In another embodiment, the pH is about 4.

The pH of the composition may be determined by any suitable method known in the art, for example, using a glass electrode pH meter or a pH indicator, such as universal indicator.

In one embodiment, the pH of the composition is such that the solubility of the glycolate in the liquid carrier is maximised. In one embodiment, the glycolate is completely soluble in the liquid carrier. In another embodiment, the glycolate is substantially soluble in the liquid carrier. In another embodiment, the glycolate is at least partially soluble in the liquid carrier. In one embodiment, the glycolate is soluble in the liquid carrier. The solubility of the glycolate in the liquid carrier can be determined, for example, by gravimetric methods.

In one embodiment, the pH of the composition is such that the preservative or biocidal or substrate modifying species, other than boron, fixes in or on or in and on the organic substrate on application of the composition to the substrate.

In one embodiment, the glycolate has a solubility of more than about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, or 85 g/L in the liquid carrier. In one embodiment, the glycolate has a solubility of more than about 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, or 90 g/L. In one embodiment, the glycolate has a solubility of more than about 1, 2, 3, 4, 5, 6, 7, 8, 9, 10, 15, 20, 30, 40, 50, 60, 70, 80 or 90 g/L. In one embodiment, the glycolate has a solubility of more than about 10, 15, 20, 30, 40, 50, 60, 70, 80, or 90 g/L.

In one embodiment, the glycolate has a solubility of less than about 250, 200, 190, 180, 170, 160, 150, 140, 130, 120, 110, or 100 g/L. In one embodiment, the glycolate has a solubility of less than about 150, 140, 130, 120, 110, or 100 g/L.

In one embodiment, the preservative or biocidal or substrate modifying species, other than boron is a preservative or biocidal species. In another embodiment, the preservative or biocidal species, other than boron, is a preservative and biocidal species. In another embodiment, preservative or biocidal species, other than boron, is a preservative species. In another embodiment, preservative or biocidal species, other than boron, is a biocidal species.

In one embodiment, the species is a metal or a non-metal, other than boron. In one embodiment, the metal or non-metal is selected from groups 4, 5, 7-12, 14, and 15 of the periodic table. In another embodiment, the metal or non-metal is selected from periods 4 and 5 in groups 4, 5, and 7-12; period 2 in group 14; and periods 5 and 6 in group 15 of the periodic table. In one embodiment, the species is selected from the group consisting of copper, zinc, iron, cobalt, manganese, antimony, bismuth, titanium, zirconium, nickel, vanadium, silver, and silicon.

In another embodiment, the species is selected from the group consisting of copper, zinc, iron, cobalt, manganese, antimony, bismuth, titanium, zirconium, nickel, vanadium, and silver.

In another embodiment, the species is copper or zinc.

In another embodiment, the species is copper.

The species may be in any suitable oxidation state. In one embodiment, the species is selected from copper (II) or zinc (II). In another embodiment, the species is copper (II).

The preservative or biocidal or substrate modifying species, other than boron, in the form of a glycolate comprises at least one glycol. The glycol comprises at least two hydroxyl groups capable of reacting with a species to form a glyolate.

In one embodiment, the glycol is a di-, tri-, or polyhydric alcohol. In one embodiment, at least two of the hydroxyl groups are in a 1,2- (i.e. vicinal) or 1,3-relationship with respect to each other capable of forming a glycolate.

In one embodiment, the glycol is a $C_2$-$C_{20}$di-, tri-, or polyhydric alcohol, a sugar, a sugar alcohol, a polymeric alcohol (e.g., a polyether alcohol, such as polyethylene glycol, polypropylene glycol, and the like), or a mixture thereof. In one embodiment, the di-, tri-, or polyhydric alcohol is a $C_2$-$C_{12}$di-, tri-, or polyhydric alcohol, a monosaccharide or a sugar alcohol derived therefrom, an oligosachamide comprising from two 2 to 10 pentose and/or hexose units or a sugar alcohol derived therefrom, a polymeric alcohol or co-polymer or block co-polymer thereof, or any mixture thereof.

In one embodiment, the glycol is a di-, tri-, or polyhydric alcohol, or a mixture thereof. In one embodiment, the di-, tri-, or polyhydric alcohol is a $C_2$-$C_{20}$alcohol. In one embodiment, the $C_2$-$C_{20}$alcohol is a $C_2$-$C_6$di-, tri-, or polyhydric alcohol, a vicinal diol, a sugar, a sugar alcohol, a polymeric alcohol or a mixture thereof.

In one embodiment, the polymeric alcohol is a polyether polymer of one or more $C_2$-$C_6$di-, tri-, or polyhydric alcohols.

In one embodiment, the sugar is a non-reducing sugar. In one embodiment, the non-reducing sugar is a di-, or trisaccharide, or a mixture thereof.

Examples of suitable glycols include, but are not limited to ethylene glycol, propylene glycol, glycerol, erythritol, sorbitol, mannitol, sucrose, galactitol, trehalose, xylitol, ribitol, and the like.

In one embodiment, the glycol is a $C_2$-$C_6$di-, tri-, or polyhydric alcohol or a polyether polymer of one or more thereof, a non-reducing di- or trisaccharide, a $C_2$-$C_{12}$sugar alcohol, or a mixture thereof.

In one embodiment, the $C_2$-$C_6$di-, tri-, or polyhydric alcohol is a lower alkylene or lower alkenylene glycol. In one embodiment, the $C_2$-$C_6$di-, tri-, or polyhydric alcohol is a lower alkylene glycol. In one embodiment, the $C_2$-$C_6$di-, tri-, or polyhydric alcohol is a lower alkylene diol or triol. In one embodiment, the glycol is selected from the group consisting of ethylene glycol, propylene glycol, glycerol, or a mixture thereof. In one embodiment, the glycol is selected from the group consisting of ethylene glycol, glycerol, or a mixture thereof.

In one embodiment, the glycol is a vicinal diol. In another embodiment, the glycol is a polyhydroxy compound. In one embodiment the glycol is a sugar or polyol.

Numerous glycols are commercially available.

In one embodiment, the liquid carrier comprises water. In one embodiment, the composition comprises at least 10%, 20%, 30%, 40%, 50%, 60%, 70%, 80%, or 90% water.

In another embodiment, the liquid carrier comprises an alcohol. In one embodiment, the alcohol is a $C_1$-$C_6$alcohol. In one embodiment, the alcohol is selected from methanol, ethanol, n-propanol, i-propanol, n-butanol, sec-butanol, iso-butanol, tert-butanol, and mixtures thereof. In one embodiment, the alcohol is selected from methanol, ethanol, n-propanol, i-propanol and mixtures thereof. In one embodiment, the alcohol is selected from the group consisting of methanol, ethanol, and mixtures thereof. In one embodiment, the alcohol is methanol. In another embodiment, the alcohol is ethanol.

In another embodiment, the liquid carrier comprises a glycol. In one embodiment, the glycol is as defined in any of the embodiments described above. In one embodiment, the glycol is selected from the group consisting of ethylene glycol, propylene glycol, glycerol, and mixtures thereof. In another embodiment, the glycol is ethylene glycol, glycerol, or a mixture thereof. In one embodiment, the glycol is ethylene glycol. In another embodiment, the glycol is glycerol.

In another embodiment, the liquid carrier comprises a mixture of water and an alcohol. In another embodiment, the liquid carrier comprises a mixture of water and an alcohol selected from the group consisting of methanol, ethanol, n-propanol, i-propanol, and mixtures thereof.

In another embodiment, the liquid carrier comprises a mixture of water and a glycol. In another embodiment, the liquid carrier comprises a mixture of water and a glycol selected from the group consisting of ethylene glycol, propylene glycol, glycerol, and mixtures thereof.

In another embodiment, the liquid carrier comprises a mixture of water, an alcohol, and a glycol. In another embodiment, the liquid carrier comprises a mixture of water, an alcohol selected from the group consisting of methanol, ethanol, n-propanol, i-propanol, and mixtures thereof, and a glycol from the group consisting of ethylene glycol, propylene glycol, glycerol, and mixtures thereof.

In one embodiment, the liquid carrier comprises ammonia or an aqueous solution of ammonia. In another embodiment, the liquid carrier comprises a mixture of water, an alcohol selected from the group consisting of methanol, ethanol, n-propanol, i-propanol, and mixtures thereof, a glycol from the group consisting of ethylene glycol, propylene glycol, glycerol, and mixtures thereof, and ammonia.

In one embodiment, the liquid carrier comprises one or more amines. In one embodiment, the liquid carrier comprises a mixture of water, an alcohol, a glycol, ammonia, and/or an amine. In one embodiment, the liquid carrier comprises a water; and an alcohol, a glycol, ammonia, an amine, or any mixture thereof.

The liquid carrier may comprise one or more additional solvents. Examples of suitable solvents include acetone, N-methylpyrrolidone, dimethylformamide, formamide, dimethylsulphoxide, glycol partial ethers, glycol diethers and the like. In one embodiment the one or more additional solvents are miscible with water.

In one embodiment, the composition further comprises one or more additional preservative or biocidal or substrate modifying species that is stable in the presence of the glycolate and at the pH of the composition.

In one embodiment, the additional species is a preservative or biocidal species. In another embodiment, the additional species is a preservative and biocidal species. In another embodiment, the additional species is a preservative species. In another embodiment, the additional species is a biocidal species.

In one embodiment, the additional species is a secondary biocide or co-biocide.

In one embodiment, the additional species is selected from the group comprising biocidal or preservative micronized species, for example, micronized copper species, biocidal or preservative metal species, for example zinc, silver and the like, and organic biocides, for example quaternary ammonium compounds, triazoles, amine oxides, thiazoles, triazoles, phthalonitriles, and the like.

Those versed in the art will be aware that any combination of preservative or biocidal or substrate modifying species can be used, as long as potential issues such as solubility and compatibility are taken into account. For example, quaternary ammonium compounds are generally facile, being soluble in water over a wide pH range, and are thus suitable as long as effects from any destabilizing cationic or anionic species are accounted for.

The additional species may be water soluble or water insoluble. Examples of additional species include organic biocides, for example fungicides, insecticides, moldicides, bactericides, algaecides etc. Organic biocides are well known to those skilled in the art and include, for example, azoles, quaternary ammonium compounds, borate compounds, fluoride compounds and combinations thereof. Examples of water soluble biocides include quaternary ammonium compounds, for example alkyldimethylbenzylammonium chloride, dimethyldidecylammonium chloride, dimethyldidecylammonium carbonate/bicarbonate and the like. Examples of water insoluble biocides include, but are not limited to, azoles, for example cyproconazole, propiconazole, tebuconazole, Busan (TCMTB), 2-(thiocyanatomethylthio), benzothiazole, chlorothalonil, and dichlofluanid, isothiazolones, for example Kathon 930, Kathon WT, methylisothiazolinone, benzisothiazolin-3-one, and 2-octyl-3-isothiazolone, imidacloprid, iodopropynyl butylcarbamate (IPBC), pyrethroids, for example, bifenthrin, cypermethrin, and permethrin, chitin, chitosan, clorpyrifos, 4-cumylphenol, fipronil, carbendazim, cyfluthrin, and 4-alpha-cumylphenol.

In one embodiment, the additional preservative or biocidal or substrate modifying species is a fungicide. In one embodiment, the fungicide is selected from the group of fungicides active against wood-rotting basidiomycetes. In one embodiment the fungicide comprises one or more fungicides selected from the group of conazoles and ergosterol biosynthesis inhibitors to prevent the growth of white rot, brown rot, and soft rot fungi, which are the major causes of wood decay in untreated wood. Examples of conazoles include climbazole, clotrimazole, imazalil, oxpoconazole, prochloraz, triflumizole, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, and uniconazole-P. Examples of ergosterol biosynthesis inhibitors include morpholine fungicides, for example aldimorph, benzamorf, carbamorph, dimethomorph, dodemorph, fenpropimorph, flumorph, and tridemorph. Examples of other fungicides that have been found to be effective against one or more wood-rotting fungi include carboxin, iprodione, fenpiclonil, ferbam, fenpiclonil, capafol, 8-hydroxyquinoline, nabam, oxycarboxin, cyprodinil, chlorothanil, axaoxystrobin, trifloxystrobin, thiram, fluazinam, terrazole, carbendazim, and benomyl. These fungicides can be used in combination with one or more conazoles or ergosterol biosynthesis inhibitors in the invention.

In another embodiment, the additional species is an insecticide. Examples of insecticides include pyrazolines, indazoles, oxyindazoles, pyrazoline carboxanilides, pyridazines, oxadiazines, tricyclic pyridazines, tricyclic oxadiazines, tricyclic triazines, carbamates, organophosphates (for example, chlorpyrifos and dichlorvos), fenvalerate, fipronil, and indoxacarb and its metabolite, and mixtures thereof.

In one embodiment, the additional species is ammonia.

In another embodiment, the additional species is a quaternary ammonium compound.

In another embodiment, the additional species is a boron glycolate. In another embodiment, the additional species is a silicon glycolate. In another embodiment, the additional species is an aluminium glycolate. In one embodiment, the additional species is a glycolate of boron, silicon, or aluminium, or a mixture thereof.

In another embodiment, the additional species is an azole compound. In one embodiment, the azole is tebuconazole or propiconazole.

In another embodiment, the additional species is an insecticide. In one embodiment the insecticide is a pyrethroid. In one embodiment, the insecticide is permethrin or bifenthrin.

In another embodiment, the insecticide is fipronil or imidacloprid.

In one embodiment, the one or more additional species is at least partially soluble in the liquid carrier.

In one embodiment, the one or more additional species is in an emulsion or a micro-emulsion with the liquid carrier. In one embodiment, the emulsion or micro-emulsion comprises one or more solvents of the one or more suitable species.

In one embodiment, the one or more additional species is in the form of micronised particles. In one embodiment, the micronised particles are dispersed in the liquid carrier. In another embodiment, the composition comprises an emulsion or micro-emulsion of the micronised particles and one or more suitable carriers in which the particles are dispersed. In another embodiment, the micronised particles are encapsulated. In one embodiment, the micronised particles are encapsulated together with one or more suitable carriers in which the particles are dispersed.

In one embodiment, the organic substrate is a lignocellulosic substrate. In one embodiment, the lignocellulosic substrate is wood, a wood product, or a wood composite. In another embodiment, the lignocellulosic substrate is lumber, a lumber product, or a lumber composite. In another embodiment, the lignocellulosic substrate is timber, a timber product, or a timber composite. In another embodiment, the lignocellulosic substrate is wood, lumber, timber or a product or composite thereof. In one embodiment, the lignocellulosic substrate is wood, lumber, or timber.

In one embodiment, the composition, when tested using the AWPA E12 corrosion standard method, compared to standard ACQ, results in an mpy that is at least 20% less. In one embodiment, the mpy is at least 30% less, at least 40% less, at least 50% less, at least 60% less, at least 70% less, at least 80% less, or at least 90% less. In one embodiment, the mpy is at least 60% less. In another embodiment, the composition exhibits no corrosion. Whilst the AWPA E12 corrosion standard method may not specify the amount of copper added to the wood, those versed in the art will know the typical incorporation rates and will also know that higher loadings will exacerbate corrosion proportionately.

In one embodiment, the composition, when tested using the AWPA A11-93 protocol, compared to standard ACQ, results in a leachate having at least 20% less of the preservative or biocidal or substrate modifying species, other than boron. In one embodiment, the leachate has at least 30% less, at least 40% less, at least 50% less, at least 60%, at least 70% less, at least 80% less at least 90% less of the preservative or biocidal or substrate modifying species, other than boron.

In one embodiment, the composition comprises at least 0.001%, 0.01%, 0.1%, 0.5%, 1%, 2%, 3%, 5%, 10%, 15%, 20%, 25%, 30%, 35%, or 50% wt/wt of the glycolates. In another embodiment, the composition comprises less than 75%, 50%, 35%, 30%, 25%, 20%, 15%, 10%, 5%, or 3% wt/wt of the glycolate. In another embodiment, the composition comprises from 0.001 to 75%, 0.001 to 50%, 0.001 to 35%, 0.001 to 30%, 0.001 to 25%, 0.001 to 20%, 0.001 to 15%, 0.001 to 10%, 0.001 to 5%, 0.001 to 3%, 0.01 to 50%, 0.01 to 35%, 0.01 to 30%, 0.01 to 25%, 0.01 to 20%, 0.01 to 15%, 0.01 to 10%, 0.01 to 5%, 0.01 to 3%, 0.1 to 35%, 0.1 to 30%, 0.1 to 25%, 0.1 to 20%, 0.1 to 15%, 0.1 to 10%, 0.1 to 5%, 0.1 to 3%, 1 to 30%, 1 to 25%, 1 to 20%, 1 to 15%, 1 to 10%, 1 to 5%, 1 to 3%, 1 to 5%, and 1 to 3% wt/wt of the glycolate.

In one embodiment, the composition is in the form of a concentrate for dilution prior to application to the substrate. In another embodiment, the composition is in a form suitable for application to the substrate without dilution.

In one embodiment, the composition comprises 10, 20, 30, 40, 50, 60, 70, 80, 90, or 95% wt/wt water or more. In another embodiment, the composition comprises from 10 to 95, 10 to 90, 10 to 80, 10 to 70, 10 to 60, 10 to 50, 10 to 40, 10 to 30, 10 to 20, 20 to 95, 20 to 90, 20 to 80, 20 to 70, 20 to 60, 20 to 50, 20 to 40, 20 to 30, 30 to 95, 30 to 90, 30 to 80, 30 to 70, 30 to 60, 30 to 50, 30 to 40, 40 to 95, 40 to 90, 40 to 80, 40 to 70, 40 to 60, 40 to 50, 50 to 95, 50 to 90, 50 to 80, 50 to 70, 50 to 60, 60 to 95, 60 to 90, 60 to 80, 60 to 70, 70 to 95, 70 to 90, 70 to 80, 80 to 95, 80 to 90, or 90 to 95% wt/wt water.

In one embodiment, the preservative or biocidal or substrate modifying species, other than boron, on application to the substrate, is retained in an amount from about 0.0001 to 10, 0.0001 to 9, 0.0001 to 8, 0.0001 to 7, 0.0001 to 6, 0.0001 to 5, 0.0001 to 4, 0.0001 to 3, 0.0001 to 2, 0.0005 to 10, 0.0005 to 9, 0.0005 to 8, 0.0005 to 7, 0.0005 to 6, 0.0005 to 5, 0.0005 to 4, 0.0005 to 3, 0.0005 to 2, 0.001 to 10, 0.001 to 9, 0.001 to 8, 0.001 to 7, 0.001 to 6, 0.001 to 5, 0.001 to 4, 0.001 to 3, 0.001 to 2, 0.005 to 10, 0.005 to 9, 0.005 to 8, 0.005 to 7, 0.005 to 6, 0.005 to 5, 0.005 to 4, 0.005 to 3, 0.005 to 2, 0.01 to 10, 0.01 to 9, 0.01 to 8, 0.01 to 7, 0.01 to 6, 0.01 to 5, 0.01 to 4, 0.01 to 3, 0.01 to 2, 0.05 to 10, 0.05 to 9, 0.05 to 8, 0.05 to 7, 0.05 to 6, 0.05 to 5, 0.05 to 4, 0.05 to 3, or 0.05 to 2 m/m.

In another aspect, the invention is, as a preservative or biocide or substrate modifier suitable for, or for, treating an organic substrate (e.g., such as wood),
   at least one preservative or biocidal or substrate modifying species, other than boron, present as a glycolate as defined herein, and
   a liquid carrier for the glycolate;
   wherein the composition has a pH greater than 9;
   and wherein the composition is at least in part aqueous insofar as the liquid carrier is concerned;
   and wherein the liquid carrier is at least a partial solvent of the glycolate;
   and wherein, optionally, at least one other preservative or biocidal or substrate modifying species, and this may be boron, is present in the liquid carrier and whether present as a glycolate or not.

In one embodiment, the preservative or biocidal or substrate modifying species glycolate includes a glycol or a mixture of glycols.

In one embodiment, the glycol is ethylene glycol, propylene glycol or glycerol.

In one embodiment, the glycol is a vicinal diol.

In one embodiment, the glycol is a polyhydroxy compound. In one embodiment, the glycol is a sugar or other polyol.

In one embodiment, the glycol is monoethylene glycol or glycerol.

In one embodiment, the glycol is glycerol.

In one embodiment, the preservative or biocidal or substrate modifying species present as a glycolate is a compound of the formula (I):

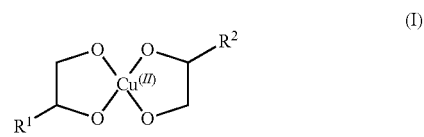

wherein:
   $R^1$ and $R^2$ are each independently selected from the group consisting of hydrogen, hydroxymethyl, alkyl, alkoxy, substituted carboxy, and the like.

In one embodiment, $R^1$ and $R^2$ are each hydrogen and the compound is copper (II) ethylene glycolate (copper (II) attached to two ethylene glycol ligands).

In another embodiment, $R^1$ and $R^2$ are each hydroxymethyl and the compound is copper (II) glycerolate.

Those skilled in the art will appreciate that the compound of formula (I) can carry a charge when in solution, particularly in the presence of a strong alkali (charge not shown). The charge may be balanced by the presence of any suitable counter-ion(s) in the necessary stoichiometry. For example, when the compound of formula (I) has a charge of −2, the anionic charge may be balanced by the presence of one divalent cation or two mono-valent cations. In one embodiment, the counter-ions are sodium cations.

In another embodiment, the preservative or biocidal or substrate modifying species is a compound of the formula (I) as defined herein, wherein the copper ion is replaced with a zinc ion.

In one embodiment, $R^1$ and $R^2$ are each hydrogen and the compound is zinc (II) ethylene glycolate.

In another embodiment, $R^1$ and $R^2$ are each hydroxymethyl and the compound is zinc (II) glycerolate.

Variations are numerous and will occur to one versed in the art, but each must allow for the oxidation state of the central moiety. For example, the compound below exists as an anion with a single negative charge (charge not shown).

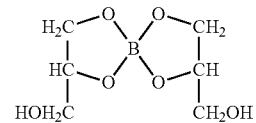

The charge is balanced by the presence of a counter ion, such as Na+. The compound can be called spiroglyceroboronate, as described in NZ 549510, but can equally be described as boron glycerolate.

Those versed in the art of coordination chemistry will be aware that transition metals in the presence of suitable ligands can form coordination complexes. For example, copper is capable of forming octahedral coordination complexes typified by a deep blue colour, as observed in the Examples described herein.

An example of an octahedral copper glycolate coordination complex is shown below. The copper glycolate complex has four bonds between the copper atom and the oxygen atoms of the two glycol ligands, therefore two additional ligands can participate in formation of the octahedral complex. Suitable additional ligands include, for example, water (as shown below), ammonia (ammine), amines, alcohols, organic acids, bidentate ligands, for example ethylenediamine, or other suitable molecules.

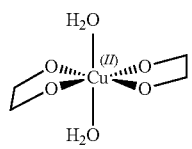

Without wishing to be bound by theory, the inventor believes that the compound prepared in Example 1 below comprises $Na_2CuC_6H_{12}O_6 \cdot 2H_2O$.

A person skilled in the art will appreciate that the different species can accommodate different numbers of ligands. The oxidation state of the species can affect the number of ligands that species can accommodate.

The oxidation state of the species and the nature of the ligands, including the glycol ligand(s), determine the overall charge of the glycolate compound. The charge may be balanced by the presence of any suitable cation or, if applicable, anion in the necessary stoichiometry. Examples of cations include metal cations, for example alkali or alkaline earth metal cations, for example lithium, sodium, potassium, magnesium, and calcium cations, transition metal cations, for example titanium, zirconium, vanadium, molybdenum, iron, cobalt, nickel cations, other metal cations, for example, zinc and copper cations, and organic cations, for example quaternary ammonium compounds. Examples of anions include inorganic anions, for example halogen anions, for example, fluorine, chlorine, bromine, and iodine anions, sulphate, phosphate, hydroxide, nitrate, carbonate, and bicarbonate anions, and organic anions, for example alkoxides, acetates, and carboxylates. Other cations and anions will be apparent to those skilled in the art.

The glycolate comprises at least one glycol. In one embodiment, the glycolate comprises two glycols. In another embodiment, the glycolate comprises three glycols.

The glycolate may further comprise one or more ligands that are not glycols. In one embodiment, the glycolate comprises one or more water ligands. In another embodiment, the glycolate comprises one or more alcohol ligands. In another embodiment, the glycolate comprises one or more ammonia or amine ligands. In one embodiment, the glycolate comprises one or more ligands selected from water, alcohol, ammonia, amine and mixtures thereof.

Sometimes it may be preferred to have a mixture of ligands. In one embodiment, such ligands might include glycols in admixture with ammonia, amines and/or water. In one embodiment, such ligands might include glycols in admixture with ammonia and/or amines. In another embodiment, such ligands might include glycols in admixture with water.

In some embodiments, the ratio of the glycol to the species (for example, copper) is from about 1:1 to about 3:1, from about 1:1 to 2:1, or about 2:1.

In one embodiment, the liquid carrier is water, or simple alcohols or mixtures thereof.

In one embodiment, the liquid carrier comprises additional glycols.

In one embodiment, the liquid carrier comprises one or more amines. Examples of suitable amines include, but are not limited to, monoethanolamine, diethanolamine, triethanolamine, ethylenediamine, and the like.

If required the liquid carrier can include dispersants and/or surfactants.

In one embodiment, the preservative or biocidal or substrate modifying species, other than boron, is selected from the group consisting of copper, zinc, iron, cobalt, manganese, antimony, bismuth, titanium, zirconium, nickel, vanadium, silver, and others.

In one embodiment, the preservative or biocidal or substrate modifying species, other than boron, is copper or zinc.

In one embodiment, the preservative or biocidal or substrate modifying species, other than boron, is copper.

In one embodiment, the composition includes one or more biocides.

In one embodiment, the composition comprises a mixture of glycolates.

In one embodiment, the composition includes a mixture of a preservative or biocidal or substrate modifying species, other than boron, as a glycolate plus a glycolate of boron.

In one embodiment, the composition includes a mixture of a preservative or biocidal or substrate modifying species, other than boron, as a glycolate plus a glycolate of silicon.

In one embodiment, the composition includes a mixture of a preservative or biocidal or substrate modifying species, other than boron, as a glycolate plus a glycolate of aluminium.

In one embodiment, the composition includes a mixture of a preservative or biocidal or substrate modifying species, other than boron, as a glycolate plus a mixture of alternative glycolate species.

In one embodiment, the composition comprises one or more compounds for adjusting the pH of the composition. In one embodiment the compound is an alkali or alkaline earth compound.

In one embodiment the alkali compound is sodium or potassium hydroxide.

In one embodiment, the compound for adjusting the pH of the composition is acetic acid or sulphuric acid.

In one embodiment, the composition comprises an additional complexing or chelating agent.

In one embodiment, the composition comprises one or more co-biocides, in addition to the preservative or substrate modifying species, other than boron, as a glycolate.

In one embodiment, the one or more co-biocides include a quaternary ammonium compound, a boron compound, a fluoride compound or an azole.

In one embodiment, the quaternary ammonium compound is a benzalkonium salt or dimethyldidecylammonium salt.

In one embodiment, the quaternary ammonium compound is a benzalkonium chloride or dimethyldidecylammonium chloride.

In another embodiment the quaternary ammonium compound is didecyldimethylammonium carbonate or bicarbonate.

In one embodiment, the azole is propiconazole or tebuconazole or a mixture of these.

In one embodiment, the boron compound is a boron glycolate compound.

In one embodiment, the composition includes an amine oxide or an alkoxylated amine.

In one embodiment the co-biocides include insecticides such as permethrin or bifentrhin or fungicides such as chlorothalonil.

In one embodiment, the co-biocides have low solubility in the preferred liquid carriers and are incorporated as micronized particles, as emulsions or micro-emulsions or as encapsulated or micro-encapsulated particles.

In one embodiment, the composition includes nano particulate biocides, micro-emulsions or micro-encapsulated biocides.

In one embodiment, the organic substrate is lignocellulosic.

In one embodiment, the lignocellulosic substrate is lumber or lumber composite.

In one embodiment, the organic substrate is lumber.

In one embodiment the lumber is sufficiently dry to allow impregnation by the composition.

In one embodiment, the substrate is lumber that is at or below fibre saturation.

In another aspect, the present invention provides a composition for treating an organic substrate comprising:
  micronised particles of a preservative or biocidal or substrate modifying species, other than boron, in the form of a glycolate; and
  a liquid carrier.

The term "micronised particles" as used herein means particles having a particle size within the range of 0.005 to 25 microns. The term "particle size" as used herein refers to the size of the largest dimension of the particle.

The preservative or biocidal or substrate modifying species, other than boron, in the form of a glycolate is as defined in any of the embodiments described above. In one embodiment, the species, other than boron, is a metal. In one embodiment, the metal is copper.

The species, other than boron, in the form of a glycolate comprises at least one glycol. The glycol is as defined in any of the embodiments described above.

In one embodiment, the micronised particles are sub-micron particles. The term "sub-micron particles" as used herein means particles having a particle size less than one micron. In one embodiment, the sub-micron particles have a particle size greater than 0.01 micron.

In one embodiment, the micronised particles are dispersed in the liquid carrier. In another embodiment, the composition comprises an emulsion or micro-emulsion of the micronised particles and one or more suitable carriers in which the particles are dispersed. In another embodiment, the micronised particles are encapsulated. In one embodiment, the particles are encapsulated together with one or more suitable carriers in which the particles are dispersed.

In one embodiment, the liquid carrier comprises water. In another embodiment, the liquid carrier comprises a mixture of water and one or more additional water-miscible or water immiscible solvents.

In one embodiment, the liquid carrier comprises one or more organic solvents.

Examples of solvents include acetone, N-methylpyrrolidone, dimethylformamide, formamide, dimethylsulphoxide, glycol partial ethers, glycol diethers, alcohols, for example $C_1$-$C_6$ alcohols, for example methanol, ethanol, n-propanol, i-propanol, n-butanol, sec-butanol, iso-butanol, tert-butanol, vegetable oils, non-polar organic solvents, and the like, and mixtures thereof.

In one embodiment, the composition further comprises one or more additional biocidal or preservative or substrate modifying species. The one or more additional species is as defined in any of the embodiments described above.

In one embodiment, the additional species is in the form of micronised particles. In one embodiment, the additional species is micronised zinc.

In one embodiment, the pH of the composition is from 4 to 11. In another embodiment, the pH of the composition is from 4.5 to 10.5. In another embodiment, the pH of the composition is from 4 to 10, from 4 to 9, from 4 to 8, from 4 to 7, from 4 to 6, from 4 to 5, from 5 to 11, from 5 to 10, from 5 to 9, from 5 to 8, from 5 to 7, from 5 to 6, from 6 to 11, from 6 to 10, from 6 to 9, from 6 to 8, from 6 to 7, from 7 to 11, from 7 to 10, from 7 to 9, from 7 to 8, from 8 to 11, from 8 to 10, from 8 to 9, from 9 to 11, from 9 to 10, or from 10 to 11.

In one embodiment, the pH of the composition is such that the micronised particles of the preservative or biocidal or substrate modifying species, other than boron, in the form of a glycolate are at least partially insoluble in the liquid carrier. In one embodiment, the micronised particles are substantially or completely insoluble in the liquid carrier.

In one embodiment, the composition comprises 10, 20, 30, 40, 50, 60, 70, 80, 90, or 95% wt/wt water or more. In another embodiment, the composition comprises from 10 to 95, 10 to 90, 10 to 80, 10 to 70, 10 to 60, 10 to 50, 10 to 40, 10 to 30, 10 to 20, 20 to 95, 20 to 90, 20 to 80, 20 to 70, 20 to 60, 20 to 50, 20 to 40, 20 to 30, 30 to 95, 30 to 90, 30 to 80, 30 to 70, 30 to 60, 30 to 50, 30 to 40, 40 to 95, 40 to 90, 40 to 80, 40 to 70, 40 to 60, 40 to 50, 50 to 95, 50 to 90, 50 to 80, 50 to 70, 50 to 60, 60 to 95, 60 to 90, 60 to 80, 60 to 70, 70 to 95, 70 to 90, 70 to 80, 80 to 95, 80 to 90, or 90 to 95% wt/wt water.

In one embodiment, the preservative or biocidal or substrate modifying species, other than boron, on application to the substrate, is retained in an amount from about 0.0001 to 10, 0.0001 to 9, 0.0001 to 8, 0.0001 to 7, 0.0001 to 6, 0.0001 to 5, 0.0001 to 4, 0.0001 to 3, 0.0001 to 2, 0.0005 to 10, 0.0005 to 9, 0.0005 to 8, 0.0005 to 7, 0.0005 to 6, 0.0005 to 5, 0.0005 to 4, 0.0005 to 3, 0.0005 to 2, 0.001 to 10, 0.001 to 9, 0.001 to 8, 0.001 to 7, 0.001 to 6, 0.001 to 5, 0.001 to 4, 0.001 to 3, 0.001 to 2, 0.005 to 10, 0.005 to 9, 0.005 to 8, 0.005 to 7, 0.005 to 6, 0.005 to 5, 0.005 to 4, 0.005 to 3, 0.005 to 2, 0.01 to 10, 0.01 to 9, 0.01 to 8, 0.01 to 7, 0.01 to 6, 0.01 to 5, 0.01 to 4, 0.01 to 3, 0.01 to 2, 0.05 to 10, 0.05 to 9, 0.05 to 8, 0.05 to 7, 0.05 to 6, 0.05 to 5, 0.05 to 4, 0.05 to 3, or 0.05 to 2 m/m.

In another aspect, the present invention provides use of a preservative or biocidal or substrate modifying species, other than boron, in the form of a glycolate for treating an organic substrate.

The preservative or biocidal or substrate modifying species, other than boron, in the form of a glycolate and the organic substrate are as defined in any of the embodiments described above.

In another aspect, the present invention provides a use of a composition comprising:
  a liquid carrier; and
  a preservative or biocidal or substrate modifying species, other than boron, in the form of a glycolate
as a preservative or biocide or substrate modifier for treating an organic substrate.

In one embodiment, the pH of the composition is such that the glycolate is at least partially soluble in the liquid carrier.

In one embodiment, the preservative or biocidal or substrate modifying species, other than boron, in the form of a glycolate is in the form of micronised particles.

In another aspect, the invention provides a use of:
- at least one preservative or biocidal or substrate modifying species, other than boron, present as a glycolate as defined herein, and
- a liquid carrier for the glycolate;
- wherein the composition has a pH greater than 9;
- and wherein the composition is at least in part aqueous insofar as the liquid carrier is concerned;
- and wherein the liquid carrier is at least a partial solvent of the glycolate;
- and wherein, optionally, at least one other preservative or biocidal or substrate modifying species, and this may be boron, is present in the liquid carrier and whether present as a glycolate or not as a preservative or biocide or substrate modifier for treating an organic substrate.

In another aspect, the present invention provides a use of a composition of the invention as a preservative or biocide or substrate modifier for treating an organic substrate.

In another aspect, the present invention provides a process for treating an organic substrate comprising applying a preservative or biocidal or substrate modifying species, other than boron, in the form of a glycolate to the substrate.

The invention also relates to a process for treating an organic substrate wherein a composition of the invention above is applied to the substrate.

In another aspect, the invention relates to a process for treating an organic substrate comprising applying a composition of the invention to the substrate.

In one aspect, the present invention provides a process for treating an organic substrate comprising applying
- at least one preservative or biocidal or substrate modifying species, other than boron, present as a glycolate as defined herein, and
- a liquid carrier for the glycolate;
- wherein the composition has a pH greater than 9;
- and wherein the composition is at least in part aqueous insofar as the liquid carrier is concerned;
- and wherein the liquid carrier is at least a partial solvent of the glycolate;
- and wherein, optionally, at least one other preservative or biocidal or substrate modifying species, and this may be boron, is present in the liquid carrier and whether present as a glycolate or not to the substrate.

In one embodiment, the composition is applied by dipping, spraying or vacuum pressure impregnation, optionally including use of the treatment process described in WO 2004/054765.

In one embodiment, the composition is applied to the substrate by dipping, deluging, spraying, or brushing. Additionally, variations of vacuum or positive pressure impregnation may be used.

In one embodiment, the composition is applied at a temperature from ambient temperature to 100° C.

In one embodiment, the composition is applied at ambient temperature.

In one embodiment, the composition is applied to the substrate using any variation of vacuum pressure impregnation.

In one embodiment, the composition is applied to the substrate using a single vacuum impregnation.

In one embodiment, the composition is applied to a substrate which is at or below fibre saturation.

In one embodiment, the preservative or biocidal or substrate modifying species, other than boron, present in the form of or as a glycolate is fixed in or on or in and on the organic substrate on applying the composition to the substrate.

In one embodiment, the pH of the organic substrate is adjusted prior to applying the composition, such that the preservative or biocidal or substrate modifying species, other than boron, present in the form of or as a glycolate is fixed in or on or in and on the organic substrate on applying the composition to the substrate.

In one embodiment, the preservative or biocidal or substrate modifying species, other than boron, present in the form of or as a glycolate is fixed in or on or in and on the organic substrate by adjusting the pH of the substrate after applying the composition to the substrate.

In one embodiment, the preservative or biocidal or substrate modifying species, other than boron, present in the form of or as a glycolate is fixed in or on or in and on the organic substrate on applying the composition to the substrate or by adjusting the pH of the substrate after applying the composition to the substrate.

In one embodiment, the process further comprises diluting the composition prior to application to the substrate.

In one embodiment, the preservative or biocidal or substrate modifying species, other than boron, is applied to the substrate in an amount sufficient to provide a substrate wherein the biocidal or substrate modifying species, other than boron, is retained in an amount from about 0.0001 to 10, 0.0001 to 9, 0.0001 to 8, 0.0001 to 7, 0.0001 to 6, 0.0001 to 5, 0.0001 to 4, 0.0001 to 3, 0.0001 to 2, 0.0005 to 10, 0.0005 to 9, 0.0005 to 8, 0.0005 to 7, 0.0005 to 6, 0.0005 to 5, 0.0005 to 4, 0.0005 to 3, 0.0005 to 2, 0.001 to 10, 0.001 to 9, 0.001 to 8, 0.001 to 7, 0.001 to 6, 0.001 to 5, 0.001 to 4, 0.001 to 3, 0.001 to 2, 0.005 to 10, 0.005 to 9, 0.005 to 8, 0.005 to 7, 0.005 to 6, 0.005 to 5, 0.005 to 4, 0.005 to 3, 0.005 to 2, 0.01 to 10, 0.01 to 9, 0.01 to 8, 0.01 to 7, 0.01 to 6, 0.01 to 5, 0.01 to 4, 0.01 to 3, 0.01 to 2, 0.05 to 10, 0.05 to 9, 0.05 to 8, 0.05 to 7, 0.05 to 6, 0.05 to 5, 0.05 to 4, 0.05 to 3, or 0.05 to 2 m/m.

In one embodiment, the process further comprises drying the substrate after application of the composition.

In another aspect, the invention provides an organic substrate treated by the process of the invention.

In another aspect, the invention is a lignocellulosic material impregnated or infused with a metal species or a non-metallic species, other than boron;
- wherein the species was supported for its impregnation or infusion in a suitable liquid carrier;
- and wherein the species was impregnated or infused as a glycolate (as defined herein);
- and wherein the species acts biocidally, as a preservative and/or as a substrate modifier in the lignocellulosic material.

In another aspect, the invention is a lignocellulosic material impregnated or infused with a metal species or a non-metallic species, other than boron;
- wherein the species was supported for its impregnation or infusion in an elevated pH aqueous environment;
- and wherein the species was impregnated or infused as a glycolate (as defined herein);
- and wherein the species acts biocidally, as a preservative and/or as a substrate modifier in the lignocellulosic material.

In one embodiment, the species is selected from the group consisting of copper, zinc, iron, cobalt, manganese, antimony, bismuth, titanium, zirconium, nickel, vanadium, silver, and silicon. In one embodiment, the species is selected from the group consisting of copper, zinc, iron, cobalt, manganese, antimony, bismuth, titanium, zirconium, nickel, vanadium, and silver. In one embodiment, the species is copper or zinc. In one embodiment, the species is copper.

In one embodiment, the elevated pH aqueous environment is at a pH above 9. In one embodiment, the elevated pH aqueous environment is at a pH above 10. In one embodiment, the elevated pH aqueous environment is at a pH above 11.

In one embodiment, the elevated pH aqueous environment includes other active(s) compatible at the pH of the elevated pH environment.

In one embodiment, the elevated pH aqueous environment includes other liquids besides water.

In one embodiment, the elevated pH aqueous environment allows delivery by impregnation or infusion of a species that fixes in the pH environment that pertains post impregnation or infusion.

In one embodiment, the lignocellulosic material, when tested using the APWA E12 corrosion standard method, compared to lignocellulosic material treated with standard ACQ, results in an mpy that is at least 20% less. In one embodiment, the mpy is at least 30% less, at least 40% less, at least 50% less, at least 60% less, at least 70% less, at least 80% less, or at least 90% less. In one embodiment, the mpy at least 60% less. In another embodiment, the mpy is at least 70% less.

In one embodiment, the lignocellulosic material, when tested using the AWPA A11-93 protocol, compared to lignocellulosic material treated with standard ACQ, results in a leachate having at least 60% less ppm of the preservative or biocidal or substrate modifying species, other than boron. In one embodiment, the leachate has at least 65% less, at least 70% less, at least 75%, at least 85% less, at least 85% less, at least 90% less, and at least 95% less than the preservative or biocidal or substrate modifying species, other than boron.

In another aspect, the invention provides a method of preparing a composition for timber treatment, wherein the composition includes a preservative or biocidal or substrate modifying species, other than boron, glycolate compound, and wherein the method includes the use of a solvent system comprising water.

In another aspect, the present invention provides a method of preparing a composition of the present invention for timber treatment, wherein the method includes the use of a solvent system comprising water.

In another aspect, the present invention provides an organic substrate comprising a composition of the present invention.

In one embodiment, the method comprises forming the preservative or biocidal or substrate modifying species, other than boron, in the form of or as a glycolate in a solvent system comprising water.

In another embodiment, the method comprises combining the preservative or biocidal or substrate modifying species, other than boron, present in the form of or as a glycolate with a solvent system comprising water.

In one embodiment, the solvent system further comprises a glycol. In another embodiment, the solvent system further comprises an alcohol. In another embodiment, the solvent system further comprises a glycol and an alcohol.

In one embodiment, the method further comprises an pH adjustment step. The pH may be adjusted to within any of the pH ranges in the embodiments described above. Compounds suitable for adjusting the pH will be apparent to those skilled in the art.

Examples include acidifying agents, for example acetic acid, sulphuric acid, and the like, basifying agents, for example sodium and potassium hydroxide, ammonia, and the like, and buffering agents.

In one embodiment, the method further comprises diluting the composition. In one embodiment, the composition is diluted to a concentration suitable for application to the organic substrate without further dilution.

It can be noted that whilst the preservative or substrate modifying species are at least partially soluble in the liquid carrier the compositions are not required to contain any ammonia or amines.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

BRIEF DESCRIPTION OF THE FIGURES

The invention will now be described with reference to the Figures in which.

DETAILED DESCRIPTION OF INVENTION

Figure 1:
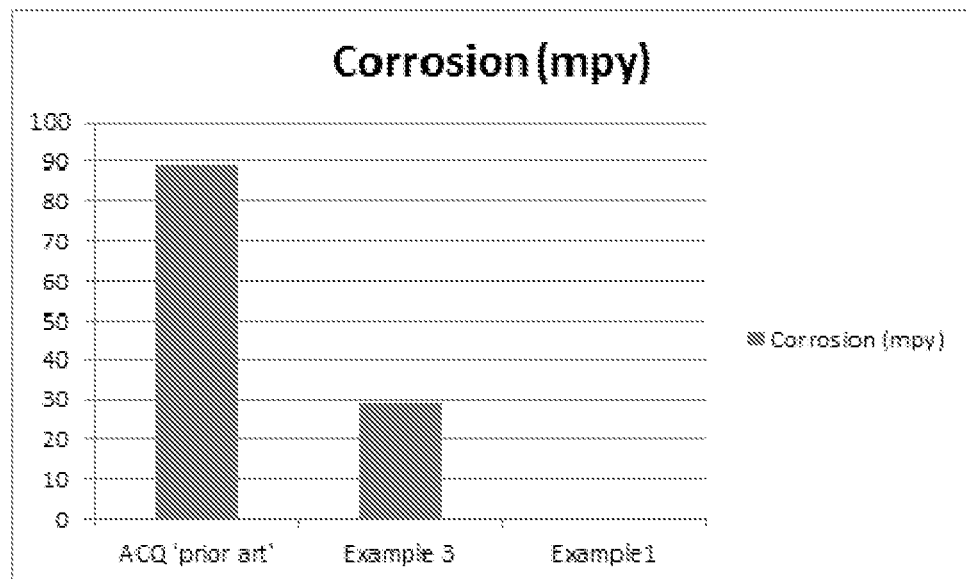
FIG. 1 is a graph showing the reduced corrosion of the composition of the invention compared to ACQ.

The following is a description of the present invention given in general terms in relation to the application of the method. While the description focuses particularly on the delivery of compositions to lignocellulosic materials, such as lumber or logs, it should be appreciated that the method may be applicable to other organic substrates.

In general terms, the invention relates to compositions for treatment of an organic substrate, for example a lignocellulosic substrate. The composition offers considerable scope in providing biocides to the substrate and mitigates the health issues of using ammonia or the cost of using amines.

The compositions of the invention may be used to impart various properties to the substrate, including biocidal protection. Persons of ordinary skill in the art to which the invention relates will no doubt appreciate various compositions that may be applicable to the invention.

By way of example, where treatment or prevention of infection or pre-infection by pest organisms is desired, compositions (biocide compositions) having pesticidal (fungicidal, bactericidal, insecticidal, for example) or preservative properties may be used.

The compositions may include compounds of use in waterproofing a substrate or providing fire retarding properties. A combination of treatment compounds (e.g. biocide and fire retardant) would clearly provide beneficial properties to the substrate.

Additionally, the compositions may contain certain dyes which may be used to colour the substrate. Suitable biocides and polymeric/prepolymeric compounds would be known to the skilled person.

Whilst not wishing to be constrained, biocides could include; copper, zinc, cobalt, boron, quaternary ammonium compounds, organo-iodine compounds, triazoles, boron compounds, insecticides such as synthetic pyrethroids and the like, or mixtures of these.

Fire retardants could include phosphorous compounds, guanidine compounds, melamine compounds, boron compounds or mixtures of these.

In certain circumstances a biocide and/or fire retardant might be used wherein the composition comprises an added emulsifier or surfactant to prepare an emulsion in the solvent combination.

As used herein, "organic substrate" should be taken to mean any organic material which may be in need of delivery of a composition of some nature; for example, for the purposes of protection or treatment to prevent or ameliorate growth of pest organisms. Such substrate may be lignocellulosic, for example living trees, wood products, lumber or logs. The invention may be applicable to substrates containing a level of moisture, or those which are substantially dry, at or below fibre saturation.

Again, at least in the case of lignocellulosic substrates, those which are "substantially dry" include lumber dried by traditional methods. Such lumber may contain moisture of approximately 1 to approximately 30 percent as a weight proportion of the lumber dry weight although in some instances the moisture content may be higher. Substantially dry lignocellulosic substrates include lumber which has been processed via kiln drying, RF vacuum drying and the like and may have been milled to a final, or near final product, and may include for example a lumber composite material.

"Pests" or "pest organisms", as referred to herein, may include any organisms which may infect an organic substrate, such as wood. While the invention is particularly applicable to fungi, pest organisms may also include insects and the like. The fungi and pests will be well known to people skilled in this art.

When used herein, the term "treatment" should be taken in its broadest possible context. It should not be taken to imply that a substrate is treated such that pest organisms are totally removed, although in some embodiments this is preferable. Prevention, for example, prophylactic treatment, and amelioration of growth of pest organisms is also encompassed by the invention. Related terms such as "treating" etc. should be interpreted in the same manner.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In one embodiment, the composition of the invention comprises a treatment fluid containing copper glycolate plus a quaternary ammonium compound in an aqueous solution at a pH which ensures solution stability, such solution being suitable for the preservation of a wood substrate against decay fungi and insects.

In one embodiment, the glycol is one or more of ethylene glycol, propylene glycol or glycerol. In another embodiment, other glycols are used.

In another embodiment of the invention, the composition comprises a copper glycerolate plus didecyldimethylammonium carbonate in an aqueous medium, wherein the pH of the composition is around 11.

In another embodiment of the invention, the composition comprises a copper glycerolate in an aqueous medium, wherein the pH of the composition is about 4 or 4.5.

In another embodiment, the composition of the invention comprises a treatment fluid containing copper glycolate plus didecyldimethylammonium carbonate in an aqueous medium in admixture with an ACQ composition wherein the final ratio of amine to copper is 1:1 as is the preferred ratio to minimise cost, corrosion, mould growth and leaching otherwise encountered with ACQ.

In another embodiment, the composition comprises copper glycolate, a quaternary ammonium salt (for example, didecyldimethylammonium carbonate), a glycol and ammonia and/or one or more amines.

In one embodiment, the glycol is one or more of ethylene glycol, propylene glycol or glycerol. In another embodiment, other glycols are used.

In another embodiment, the composition of the invention comprises a treatment fluid containing copper glycolate plus didecyldimethylammonium carbonate in an aqueous medium in admixture with a boron glycolate composition as described in NZ 549510. Surprisingly such compositions incorporating both copper and boron are stable solutions and yet need not contain any ammonia or amines.

The composition may be applied to a surface of the substrate using any known means of bringing a composition into contact with a material. By way of example, the composition is applied by dipping, deluging, spraying, or brushing.

While the inventor does not believe it necessary to apply active pressure to effect delivery of a composition in accordance with the invention, there may be instances where active pressure systems (positive pressure or vacuum) may be used to assist with delivery. Reference is made to the delivery system described in WO 2004/054765 in this regard by way of example.

While the operating temperature of the composition may vary depending on the nature of the glycolate and liquid carrier, for example its solubility and the like, the composition may be applied at or around ambient temperature. Temperatures of up to 100° C. could be used depending on the components of the composition. Higher temperatures, however, add to energy costs.

As mentioned hereinbefore, the method of the present invention is applicable to substrates which are substantially dry (i.e. at or below fibre saturation). In one embodiment, the composition is applied to the substrate which is at or below fibre saturation.

In known art, compositions which are water soluble are typically applied as fully aqueous solutions which significantly rewet the substrate. Where this wetting occurs, the subsequent removal of this water is problematic. A feature of the present invention is that it can be used at low uptakes and thus provides a useful choice for treating a substrate, where controlling or limiting rewetting of the substrate is required.

The outcome is that a preservative or substrate modifying species composition can be created with similar components to those now generically available, while reducing cost and mitigating effects of what otherwise might be classified as unessential components.

The quantity of composition used and/or the content of the glycolate in the composition may be selected to provide the desired level of treatment.

In some embodiments, the composition of the invention is used to impregnate or infuse the organic substrate with the species.

In many countries there are treatment standards for timber (for example, NZ3640) that set out the requirements for penetration of preservatives into the wood and retention of a given level of preservative for each hazard class. The higher the level of risk or hazard class the greater the level of retention required. For ACQ-type preservatives, copper retention is typically about 0.22% m/m, 0.7% m/m, and 0.9% m/m for H3.2, H4, and H5 timber, respectively. Advantageously, in some embodiments, the composition of the present invention is used to provide timber with comparable retention.

In other embodiments, the composition of the invention is applied to the surface of the organic substrate as a prophylactic treatment.

The compositions of the present invention may be prepared by any suitable method known in the art.

In one embodiment, the compositions are prepared according to a method of the present invention. The method includes the use of a solvent system comprising water. The preservative or biocidal or substrate modifying species, other than boron, present in the form of or as a glycolate may be formed in the solvent system or combined with the solvent system after formation.

The glycolate may be prepared by reacting a species with a glycol to form the glycolate. In one embodiment, the species and the glycol are reacted in the presence of a base, for example sodium or potassium hydroxide, to form the glycolate. Other methods of preparing the glycolate will be apparent to those skilled in the art.

The species and glycol may be reacted in the liquid carrier. Alternatively, the glycolate can be combined with one or more solvents to provide the liquid carrier after formation.

The method may optionally comprise a pH adjustment step to increase or decrease the pH of the composition prior to application of the composition to the organic substrate.

EXAMPLES

The following non-limiting examples are provided to illustrate the present invention and in no way limit the scope thereof.

Example 1

2.2 g (0.01 mol) Basic copper carbonate equivalent to 0.02 mol copper was added to a reaction vessel. To this was added 3.8 g (0.04 mol) glycerol plus 20 ml water giving a pale green opaque suspension. With agitation 1.6 g (0.04 mol) sodium hydroxide was slowly added until all the basic copper carbonate was dissolved resulting in a deep blue solution. The copper species was present as a copper glycerolate.

To an aliquot of this solution was added an appropriate amount of didecyldimethylammonium chloride to yield a composition matching the typical composition of ACQ in terms of copper and quaternary ammonium compound.

A specimen of kiln dried flat sawn clear *Pinus radiata* of cross section 19 mm by 150 mm was impregnated according to the method of WO 2004/054765 using a very short schedule of less than one minute. The uptake was around 40 liters of fluid per cubic meter. The specimen was subsequently cut across the section and spot tested with pyridylazonaphthol solution to show the copper distribution.

Whilst it was clear that the main path into the wood was through the ray parenchyma, the sample was completely penetrated and preservative was uniformly distributed across the whole section demonstrating a high level of treatment.

A sample of the treated wood was placed in a similar volume of water. After leaching for a period of 24 hours the water had a pH of 7.0. Wood has a natural pH of between 4 and 5. Thus the wood had neutralised alkali from the treatment solution to reduce the pH from 11 to 7.

Example 2

2.2 g (0.01 mol) Basic copper carbonate equivalent to 0.02 mol copper was added to a reaction vessel. To this was added 3.8 g (0.04 mol) glycerol plus 20 ml water giving a pale green opaque suspension. With agitation sodium hydroxide was slowly added until all the basic copper carbonate was dissolved resulting in a deep blue solution. The copper species was present as a copper glycerolate.

To this was added an equal volume of a product branded SureBor N as prepared by the method of NZ 549510 and which contained 15% by weight of boric acid equivalent with the boron present as a glycolate or spiroboronate.

The resulting composition was a stable deep blue solution.

Example 3

2.2 g (0.01 mol) Basic copper carbonate equivalent to 0.02 mol copper was added to a reaction vessel. To this was added 3.8 g (0.04 mol) glycerol plus 20 ml water giving a pale green opaque suspension. With agitation sodium hydroxide was slowly added until all the basic copper carbonate was dissolved resulting in a deep blue solution. The copper species was present as a copper glycerolate.

To this was added a quantity of monoethanolamine based ACQ solution, prepared according to AWPA P5-95 ACQ Type D, which comprises copper solubilised using monoethanolamine in a molar ratio of approximately 4 to 1 of monoethanolamine to copper, plus didecyldimethylammonium chloride co-biocide.

The ratio of copper glycolate solution to ACQ TypeD was adjusted such that the overall stoichiometric ratio of copper to amine was 1:1, which appears to be preferred for biocidal efficacy.

The resulting composition was a clear deep blue solution.

In this example the amount of amine (monoethanolamine) used is reduced by 75 percent compared to ACQ based on AWPA ACQ Type D by replacing the amine with glycerol. This results in a cost saving of around 25 to 30 percent and achieves the 1:1 stoichiometric ratio of amine to copper preferred for good fixation of copper into the substrate.

The copper glycolate in this example has a mixed ligand system. The glycolate is a copper aquo amino bisglycolate. The copper is chelated by two glycol ligands, one water ligand, and one amino ligand (monoethanolamine).

Example 4

5.0 g (0.02 mol) Cupric sulphate pentahydrate equivalent to 0.02 mol copper was added to a reaction vessel. To this was added 3.8 g (0.04 mol) glycerol plus 20 ml water giving a pale green opaque suspension. With agitation sodium hydroxide was slowly added until all the copper sulphate was dissolved resulting in a deep blue solution. An increased amount of sodium hydroxide was required (compared to, for example, Example 1) to neutralise the sulphate counter ion in the cupric sulphate. The resulting composition was a clear deep blue solution. The copper species was present as a copper glycerolate.

To an aliquot of this solution was added an appropriate amount of didecyldimethylammonium chloride to yield a composition matching the typical composition of ACQ in terms of copper and quaternary ammonium compound.

Thus a preservative solution can be prepared by this method which will include sodium sulphate as a by-product. The preservative can be used as is or the sodium sulphate can be removed. The important issue is that the preservative can be prepared from the primary and least expensive copper feedstock.

Example 5

1.6 g (0.02 mol) Cupric oxide equivalent to 0.02 mol copper was added to a reaction vessel. To this was added 3.8 g (0.04 mol) glycerol plus 20 ml water giving a pale green opaque suspension. With agitation sodium hydroxide was slowly added until all the cupric oxide was dissolved. The resulting composition was a clear deep blue solution. The copper species was present as a copper glycerolate.

Cupric oxide is frequently prepared independently of the sulphate route and thus is frequently cost effective when making preservatives. Thus this composition facilitates use of another competitive feedstock.

To an aliquot of this solution was added an appropriate amount of didecyldimethylammonium chloride to yield a composition matching the typical composition of ACQ in terms of copper and quaternary ammonium compound.

Example 6

1.95 g (0.02 mol) Cupric hydroxide equivalent to 0.02 mol copper was added to a reaction vessel. To this was added 3.8 g (0.04 mol) glycerol plus 20 ml water giving a pale green opaque suspension. With agitation sodium hydroxide was slowly added until all the cupric hydroxide was dissolved resulting in a deep blue solution. The resulting composition was a clear deep blue solution. The copper species was present as a copper glycerolate.

To an aliquot of this solution was added an appropriate amount of didecyldimethylammonium chloride to yield a composition matching the typical composition of ACQ in terms of copper and quaternary ammonium compound.

Example 7

It is known that, for example, copper metal can be oxidised in a chemical medium to prepare soluble species. This can be done for example using air in sulphuric acid to produce copper sulphate, or in ammonia to produce copper ammines or cupric oxide.

The process of oxidation of pure copper or scrap metal can also take place in a glycol solution containing alkali resulting in the required glycolate. The process may be slower than by the aforementioned direct methods but can offer a less costly means for one requiring such process. The process can be enhanced by addition of an oxidising agent such as hydrogen peroxide.

Example 8

Because corrosion is of significant concern with lumber treated with soluble copper containing preservatives, and more specifically lumber treated with traditional ACQ preservatives, the inventor undertook a corrosion study based on the accepted standard AWPA E12-94 wherein steel coupons were sandwiched between samples of treated wood and maintaining appropriate moisture content within the wood samples.

After 100 hours the steel coupons in contact with the ACQ treated wood showed significant degradation. The coupons were significantly covered with rust and the rust had migrated over the surface of the treated wood.

The steel coupons in contact with the equivalent composition of this invention showed no visual sign of corrosion and there was no change in appearance of the wood in contact with the coupons. This was quite surprising because the wood had been treated with a soluble copper complex. It was also surprising that corrosion did not occur because the quaternary ammonium compound used included chloride as the counter ion.

Example 9

Whilst corrosion of fixtures used with lumber treated with ACQ is a significant problem, when treatment plants, typically made of mild steel are exposed to ACQ, corrosion of the plant is also consequential. To establish whether corrosion might be an issue in mild steel treatment plants steel coupons were placed directly into solutions containing the preservatives described herein.

After 4 days in contact with generic ACQ coupons showed evidence of corrosion. This was manifest in particular as rust deposits at the interface between the coupons and the glass container.

It was surprising that no corrosion was visible with the composition of this invention. Again, this was surprising because the composition contained quaternary ammonium compound with chloride as the counter ion.

Example 10

To establish the relative level of leaching occurring from treated wood the inventor placed two samples of similarly treated wood into a similar volume of water.

The samples were then subject to a static leaching.

After 4 hours the wood sample treated with generic amine based ACQ leached 100 ppm of copper into the water in 4 hours. The sample treated with the product of this invention leached 20 ppm in 100 hours.

Example 11

A sample of soluble copper glycerolate was prepared as in Example 1. The pH was slowly reduced to 7 using acetic acid to yield a fine precipitate of free copper glycerolate. This demonstrates the copper glycerolate has low solubility in water at neutral pH.

Those versed in the art will appreciate that by careful manipulation of conditions during precipitation and the addition of dispersants if required, the precipitate can be obtained as a dispersion of micronised or sub-micronised particles.

Those versed in the art will also appreciate that the precipitate can be milled to provide micronised or sub-micron particles, for example, by using the methods in WO 2007/002156.

Ethanol was added to a small sample of the precipitated copper glycolate. The copper glycerolate was almost insoluble.

Samples of the precipitated copper glycolate were added to N-methylpyrrolidone, a very strong solvent, dimethylsulphoxide, also a strong solvent, and butoxyethanol. The copper glycerolate was slightly soluble in these solvents, but not highly soluble in any.

Solubility has implications for leaching, corrosion and fixation in the context of wood treatments.

Example 12

A sample of the precipitated copper glycolate prepared in Example 11 was suspended in water and the pH slowly reduced with sulphuric acid. At a pH of or around 4 the copper glycolate re-dissolved. This shows that the copper glycolate is relatively insoluble from about pH 4.5 to about pH 10.5.

Solubility is important when the compositions of this invention are used to preserve organic substrates. The compositions of the present invention can have very low solubility at neutral pH, which provides resistance to leaching and corrosion, but significant solubility at acidic pH, such as that created by degrading fungi.

This example confirms that the copper glycerolate complex can become biologically available when attack by a degrading organism arises, unlike for example the copper oxalate complex, which remains insoluble at acidic pH.

In many use situations, particularly wood preservation, use of a solution of copper glycolate at a pH of 11 is convenient because the treated wood buffers the preservative to a pH of around 7, causing fixation of the preservative in the wood.

However, in some circumstances a user may choose to use an acidic solution of the copper glycolate, for example, a solution at pH 4, and allow the pH of the wood to buffer the pH of the solution higher, thus causing a level of fixation.

Alternatively, the pH could be adjusted higher to fix the composition into the wood separately, by for example the application of an alkaline material to the wood subsequent to treatment.

Example 13

A sample was prepared as in Example 1, with the exception that the water was replaced with methanol. A clear deep blue solution resulted. This solution was mixed in various ratios with a sample prepared as in Example 1. The two solutions were miscible in a wide range of proportions.

Example 14

A sample was prepared as in Example 1, with the exception that the water was replaced with ethanol. A clear deep blue solution resulted. This solution was mixed in various ratios with a sample prepared as in Example 1. The two solutions were miscible in a wide range of proportions.

Example 15

A sample as prepared in Example 1 was mixed in various ratios with an aqueous micro-emulsion comprising a mixture of tebuconazole, propiconazole and permethrin. The resulting clear blue fluids demonstrate that the biocides are miscible in a wide range of proportions.

Example 16

Samples of wood were treated with three different soluble copper species all to the same copper retention; ethanolamine based ACQ, compositions of this invention wherein a copper to amine ratio was 1:1, and compositions of this invention free of any ammonia or amine. Steel coupons were tested for corrosion using a variation of APWA E12 corrosion standard method in which the temperature of exposure was 26° C. (instead of 49° C.) and the exposure period was 30 days (instead of 10 days).

Coupons exposed to wood treated with ACQ had a loss to corrosion of 89 mpy, 1:1 amine had a loss of 29 mpy and the amine free showed no corrosion (see FIG. 1). This confirms the reduced corrosivity of compositions of this invention.

Example 17

Samples of wood were treated to a similar copper retention using various compositions according to this invention for subsequent biological testing using the soil block or Sutter block method. The blocks were leached according to AWPA A11-93 protocol.

Figure 2:
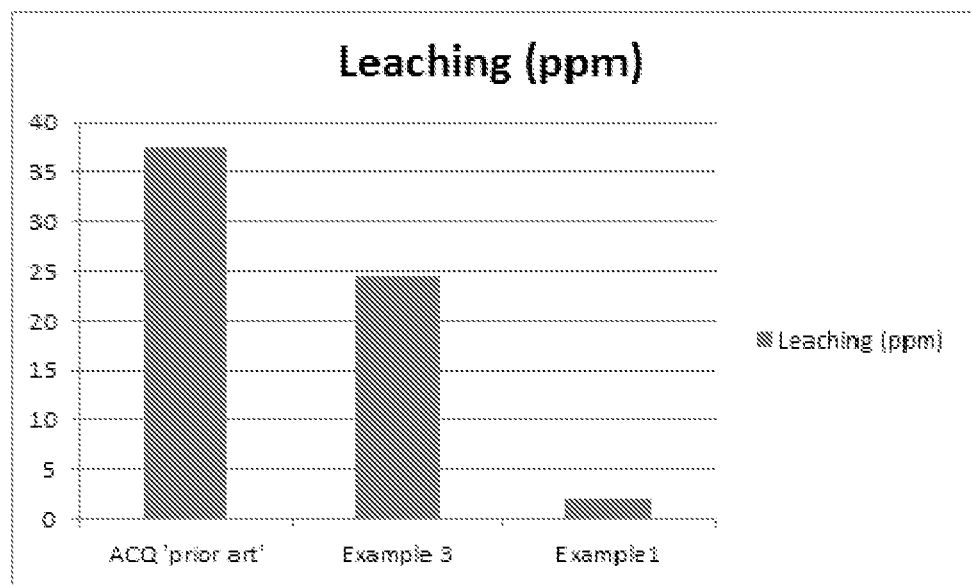
FIG. 2 is a graph showing the reduced leaching of the composition of the invention compared to ACQ.

Leachate was analysed for copper using AAS. ACQ leached 37.59 ppm copper, samples treated with composition disclosed in Example 3 leached 24.43 ppm and samples treated in accordance with Example 1 leached 2.23 ppm (see FIG. 2). Thus compositions of this invention can significantly reduce leaching of copper into the environment.

Example 18

To evaluate the compositions of this invention as biocidal preservatives a recognised independent laboratory to undertook studies in wood preservation. The studies were known as Sutter block or soil block tests. In the tests small treated wood samples were exposed to several individual fungal species for 3 months in an environment conducive to rapid fungal growth and wood degradation. Compositions of Example 1 and Example 3 were compared to ACQ Type D. The wood specimens were treated with solutions of equal copper concentration to a New Zealand Standard H3.2 except for Example 3 which had retentions 15 percent lower. The results are provided in the table below.

| Formulation | % weight loss | | |
|---|---|---|---|
| | Oligoporous placenta | Coniophora puteana | Antrodia xantha |
| Example 1 | 1.60 | 2.62 | 0 |
| Example 3 | 0.25 | 0.80 | 0 |
| ACQ Type D | 0.44 | 0.95 | 0 |
| Untreated control | 26.12 | 21.86 | 16.76 |

The composition of Example 3 comprising 1:1 amine: copper has superior performance to ACQ Type D and all samples are significantly superior to the untreated control.

Example 19

The earliest ACQ compositions included ammonia, which is a toxic gas damaging to living things and the environment. Whilst use of ammonia can give benefits when treating some wood species it is rarely used because of its toxic effects.

A sample was prepared as in Example 3, with the exception that the monoethanolamine was replaced with ammonia. A deep blue transparent solution was obtained in which the copper to ammonia ratio was 1:1.

Compared to traditional ACQ compositions, comprising ammonia, the amount of ammonia used to prepare the soluble copper based preservative in this example is reduced by 75 percent (the ammonia being replaced by the glycerol ligands).

Whilst ammonia is a very inexpensive raw material, because of its toxicity and volatility, it is less used. This example demonstrates that ammonia can be used in the present invention at a significantly lower rate. This significantly reduces cost and, concurrently, health and safety issues.

Example 20

A sample as prepared according to Example 19 was mixed with an equal amount of a composition prepared according to Example 3. A clear transparent deep blue solution with a ligand ratio of 1:1 ammonia to monoethanolamine was obtained.

Example 21

A sample was prepared as in Example 1, with the exception that glycerol was replaced with ethylene glycol in the required mol ratio.

A clear deep blue solution was obtained.

Example 22

A sample was prepared as in Example 1, with the exception that glycerol was replaced with sucrose in the required mol ratio. A deep blue solution was obtained.

Example 23

A sample was prepared using a procedure similar to that in Example 1. The quantity of water was significantly reduced.

1 g Cupric hydroxide was mixed with 1.9 g glycerol plus 0.8 g sodium hydroxide in 4 g water. A deep blue solution with copper content of 8.5 percent by weight was obtained. The copper content is in the same order as commercially available ACQ Type D.

Without wishing to be bound by theory, the inventor believes that the deep blue colour of the solutions prepared in the Examples is due to the presence of an octahedral copper complex. The complex remains stable in solution at elevated pH. When infused into wood, the pH declines and a change in colour within the wood from deep blue to pale green is observed. Without wishing to be bound by theory, the inventor believes that the octahedral complex soluble at high pH no longer exists after infusion and that the wood is infused with an insoluble copper glycolate complex.

The inventor has surprisingly shown that organic substrates, such as wood, can be treated with the composition of this invention. The preservative or biocidal or substrate modifying species, other than boron, is substantially retained within the substrate by means of substrate buffering and yet is capable of becoming biologically available should attack by a degrading organism occur.

It is clear the product of this invention confers significantly lower leaching than the generic ACQ product. This offers a potential performance benefit and a significant environmental benefit.

Thus it can be seen that compositions of this invention can readily treat substrates without necessarily using high uptakes and wherein ammonia or amine levels have been significantly reduced. In the case of treatment of lumber the amine content has been reduced to an optimum ratio reducing cost whilst, concurrently, corrosion and leaching have been significantly reduced.

The benefits of this process and composition are that treatment can be achieved very rapidly depending on the treatment process used. As described herein one method can treat a substrate in one minute or thereabouts.

Thus it can be seen that the inventor has discovered a composition which allows the treatment of substrates with chelates of elements without the need to use expensive amounts of ammonia or amines, but if desired the ammonia or amines can be limited to a stoichiometrically optimum level.

Choices of biocidal combinations of the present invention should take account of solubility and compatibility in the environment of the delivery system and the substrate to be treated. US 2004/011065, whilst not dealing with compositions of the present invention, discloses options as biocides to micronized copper species.

Where, in the foregoing description, reference has been made to components having known equivalents, then such equivalents are incorporated herein as if individually set forth.

Although the invention has been described by way of example with reference to specific embodiments, modifications and variations may be made to the invention without departing from the scope or spirit of the invention.

The invention claimed is:

1. A composition for treating a lignocellulosic substrate comprising:
   a liquid carrier; and
   a preservative or biocidal species, other than boron, in the form of a glycolate, wherein the glycolate is a compound of the preservative or biocidal species, other than boron, and at least one glycol that does not comprise a carboxylic acid, and wherein the preservative or biocidal species is copper (II); and
   one or more additional preservative or biocidal species that is stable in the presence of the glycolate and at the pH of the composition;
   wherein the pH of the composition is 9 or more and the glycolate is soluble in the liquid carrier, and
   wherein the composition comprises at least 0.5% wt/wt of the glycolate.

2. The composition of claim 1, wherein the glycol is a $C_2$-$C_6$ di-, tri-, or polyhydric alcohol or a polyether polymer of one or more thereof, a non-reducing di- or trisaccharide, a $C_2$-$C_{12}$ sugar alcohol, or a mixture thereof.

3. The composition of claim 2, wherein the glycol is selected from the group consisting of ethylene glycol, glycerol, or a mixture thereof.

4. The composition of claim 1, wherein the liquid carrier comprises water, an alcohol, a glycol, ammonia, or an amine.

5. The composition of claim 4, wherein the alcohol is selected from the group consisting of methanol, ethanol, and mixtures thereof.

6. A process for treating a lignocellulosic substrate comprising applying to the substrate a composition comprising:
   a preservative or biocidal species, other than boron, in the form of a glycolate to the substrate, wherein the glycolate is a compound of the preservative or biocidal species, other than boron, and at least one glycol that does not comprise a carboxylic acid, and wherein the preservative or biocidal species is copper (II); and
   a liquid carrier;
   wherein the pH of the composition is 9 or more and the glycolate is at least partially soluble in the liquid carrier.

7. The process of claim 6, wherein the substrate is lumber that is at or below fibre saturation.

8. The process of claim 6, wherein the preservative or biocidal species, other than boron, is fixed in or on or in and on the organic substrate on applying the composition to the substrate.

9. A composition for treating an organic substrate comprising:
- a liquid carrier comprising ammonia or an amine; and
- a preservative or biocidal species, other than boron, in the form of a glycolate, wherein the glycolate is a compound of the preservative or biocidal species, other than boron, and at least one glycol that does not comprise a carboxylic acid, and wherein the preservative or biocidal species is copper (II);
- wherein the pH of the composition is 9 or more and the glycolate is at least partially soluble in the liquid carrier.

10. The composition of claim 9, wherein the glycol is a $C_2$-$C_6$ di-, tri-, or polyhydric alcohol or a polyether polymer of one or more thereof, a non-reducing di- or trisaccharide, a $C_2$-$C_{12}$ sugar alcohol, or a mixture thereof.

11. The composition of claim 10, wherein the glycol is selected from the group consisting of ethylene glycol, glycerol, or a mixture thereof.

12. The composition of claim 9, wherein the liquid carrier further comprises water, an alcohol, or a glycol.

13. The composition of claim 12, wherein the alcohol is selected from the group consisting of methanol, ethanol, and mixtures thereof.

14. The process of claim 6, wherein the glycol is selected from the group consisting of ethylene glycol, glycerol, or a mixture thereof.

15. The process of claim 6, wherein the liquid carrier comprises water, an alcohol, a glycol, ammonia, or an amine.

16. The process of claim 6, wherein the composition is a composition according to claim 1.

17. The process of claim 6, wherein the composition is a composition according to claim 9.

* * * * *